(12) United States Patent
Bernskoetter et al.

(10) Patent No.: US 9,371,347 B2
(45) Date of Patent: Jun. 21, 2016

(54) DPPF-LIKE COMPOUNDS AND METHOD OF MANUFACTURE AND USE

(71) Applicant: BROWN UNIVERSITY, Providence, RI (US)

(72) Inventors: Wesley Hans Bernskoetter, Warwick, RI (US); Dong Jin, Providence, RI (US)

(73) Assignee: Brown University, Providence, RI (US)

( * ) Notice: Subject to any disclaimer, the term of this patent is extended or adjusted under 35 U.S.C. 154(b) by 0 days.

(21) Appl. No.: 14/768,591

(22) PCT Filed: Feb. 18, 2014

(86) PCT No.: PCT/US2014/016769
§ 371 (c)(1),
(2) Date: Aug. 18, 2015

(87) PCT Pub. No.: WO2014/130410
PCT Pub. Date: Aug. 28, 2014

(65) Prior Publication Data
US 2016/0002274 A1    Jan. 7, 2016

Related U.S. Application Data

(60) Provisional application No. 61/766,923, filed on Feb. 20, 2013.

(51) Int. Cl.
| | | |
|---|---|---|
| C07F 17/02 | (2006.01) | |
| C07C 57/04 | (2006.01) | |
| C07F 15/04 | (2006.01) | |
| C07F 19/00 | (2006.01) | |

(52) U.S. Cl.
CPC ............... *C07F 17/02* (2013.01); *C07C 57/04* (2013.01); *C07F 15/04* (2013.01); *C07F 19/00* (2013.01)

(58) Field of Classification Search
CPC ................................ C07F 17/02; C07F 19/00
USPC .......................................................... 556/7
See application file for complete search history.

(56) References Cited

U.S. PATENT DOCUMENTS

2011/0218359 A1    9/2011   Limbach et al.

FOREIGN PATENT DOCUMENTS

WO           93/21238 A2    10/1993

OTHER PUBLICATIONS

Lee, Syt. Synthesis of acrylic acid derivatives from carbon dioxide and ethylene mediated by 1-6 molecular nickel complexes. Technischen Universitat Munchen, Ph.D. dissertation, 2012, pp. 1-104 [online], [retrieved on Apr. 16, 2014]. Retrieved from the Internet <URL: http://mediatum.ub.tum.de/doc/1121436/1121436.pdf>; p. 2, paragraph 1; p. 27, paragraph 1, table 3.1a, line 12; p. 44, paragraph 1, figure 3.3a, compound C.

Bradshaw, JD et al. Planar Platinum Metallacyclynes Containing One and Two Trialkyne 1-5 Pockets. Organometallics. vol. 15, No. 11, 1996, pp. 2582-2584 [online]. [retrieved on Apr. 16, 2014]. Retrieved from the Internet <URL: http://pubs.acs.org/doilabs/10.1021/om9507 437>; abstract.

Parks, OJ et al. Synthesis and Solution and Solid-State Structures of Tris(pentafluorophenyl) 1-5 borane Adducts of PhC(O)X (X H. Me, OEt, NPri2). Organometallics, vol. 17, No. 7, 1998, pp. 1369-1377 [online]. [retrieved on Apr. 16, 2014]. Retrieved from the Internet <URL: http:/lpubs.acs.org/doi/abs/10.1 021/om971 0327>; abstract.

Lee, Syt et al. Transformation of Nickelalactones to Methyl Acrylate: on the Way to a Catalytic 6 Conversion of Carbon Dioxide. ChemSusChem, vol. 4,Iss. 9, Sep. 19, 2011, pp. 1275-1279 [online], [retrieved on Apr. 16, 2014]. Retrieved from the Internet <URL: http://onlinelibrary.wiley.com/doi/1 0.1 002/cssc.201 000445/abstract> <DOI: 10.1002/cssc.201000445>; abstract, scheme.

International Search Report dated May 12, 2014, issued in International Application No. PCT/US14/16769.

Bruckmeier, Christian et al. "Formation of Methyl Acrylate from CO2 and Ethylene via Methylation of Nickelalactones," Organometallics 2010, 29, 2199-2202.

Kurosawa, Hideo et al. "Fundamentals of Molecular Catalysis," Current Methods in Inorganic Chemistry; vol. 3, pp. 1-537.

Fischer, R. et al. "A key step in the formation of acrylic acid from CO2 and ethylene: the transformation of a nickelalactone into a nickel-acrylate complex," Chem Commun (Camb). Jun. 21, 2006; (23):2510-2.Epub May 9, 2006.

Zhang, Guoqi et al. "Mild and Homogeneous Cobalt-Catalyzed Hydrogenation of C=C, C=O, and C=N Bonds," Angewandte Chemie, Supporting Information, pp. 1-69.

(56) References Cited

OTHER PUBLICATIONS

Lejkowski, Michael L. et al. "The First Catalytic Synthesis of an Acrylate from CO2 and an Alkene—a Rational Approach," Chem. Eur. J. 2012, 18, 14017-14025.

Langer, Jens et al. "Low-Valent Nickel and Palladium Complexes with 1,1'-Bis(phosphanyl)-ferrocenes: Syntheses and Structures of Acrylic Acid and Ethylene Complexes," Eur. J. Inorg. Chem. 2007, 2257-2264.

Organometallic HyperTexBook: Beta-Hydride Elimination, Chemglass Apparatus, http://www.ilpi.com/organomet/betahydride.html, 2 pp, (2013).

Jin, Dong et al. "Lewis Acid Induced B-Elimination from a Nickelalactone-Efforts Toward Acrylate Production from CO2 and Ethylene," The Department of Chemistry, Brown University, Providenc, RI and the Department of Chemistry, Yale University, New Haven, RI, pp. 1-22.

Wikipedia, Beta-Hydride elimination, http://en.wikipedia.org/wiki/Beta_elimination, 2 pp, (2013).

*Primary Examiner* — Porfirio Nazario Gonzalez

(57) ABSTRACT

A method of β-hydride elimination and subsequent 2,1-insertion from a transient nickel(II) acrylate hydride intermediate (Structure I).

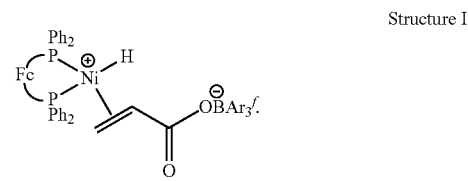

Structure I

Also addressed is treatment of (dppe)Ni(CH(CH$_3$)CO$_2$BAr$^f_3$) with a nitrogen containing base to produce a diphosphine nickel(0) η$^2$-acryl borate adduct.

9 Claims, No Drawings

DPPF-LIKE COMPOUNDS AND METHOD OF MANUFACTURE AND USE

CROSS REFERENCE TO RELATED APPLICATIONS

This is a national stage application under 35 U.S.C. §371 of International Application No. PCT/EP2014/016769, filed Feb. 18, 2014, and claims the benefit of U.S. Provisional Application No. 61/766,923, filed Feb. 20, 2013, the disclosures of all of which are incorporated herein by reference.

STATEMENT OF GOVERNMENTAL RIGHTS

This invention was made with government support awarded by the National Science Foundation under the Center for Chemical Innovation "$CO_2$ as a Sustainable Feedstock for Chemical Commodities" (CHE-1240020). The government has certain rights in the invention.

FIELD OF THE INVENTION

Disclosed is a method of β-hydride elimination and subsequent 2,1-insertion from a transient nickel(II) acrylate hydride intermediate (Structure I).

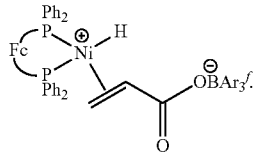

Structure I

Also addressed is treatment of $(dppe)Ni(CH(CH_3)CO_2BAr^f_3)$ with a nitrogen containing base to produce a diphosphine nickel(0) $\eta^2$-acryl borate adduct such as Structure B:

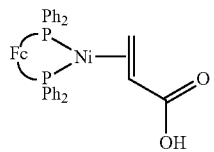

B where Fc is ferrocene;
where Ph is a phenyl group
where P is phosphorus;
where $Ar^f$ is a fluorinated aryl substituent;
where B in $BAr^f_3$ is a boron linked to three fluorinated aryl substituents;
where aryl refers to a functional group or substituent derived from an aromatic ring; and,
where superscript f references a haloginated aryl, phenyl, naphthyl, thienyl, or indolyl with at least one halogen; and,
where $R^1$ is, for example, $C_1$-$C_{12}$-alkyl such as methyl, ethyl, 1-propyl, 2-propyl, 1-butyl, 2-butyl, 1-(2-methyl)propyl, 2-(2-methyl)propyl, 1-pentyl, 1-(2-methyl)pentyl, 1-hexyl, 1-(2-ethyl)hexyl, 1-heptyl, 1-(2-propyl)heptyl, 1-octyl, 1-nonyl, 1-decyl, 1-undecyl, 1-dodecyl, $C_3$-$C_{10}$-cycloalkyl which is unsubstituted or may bear a $C_1$-$C_4$-alkyl group, for example cyclopentyl, methylcyclopentyl, cyclohexyl, methylcyclohexyl, cycloheptyl, cyclooctyl and norbornyl, aryl which is unsubstituted or may bear one or two substituents selected from chlorine, $C_1$-$C_8$-alkyl and $C_1$-$C_8$-alkoxy, such as phenyl, napthyl, tolyl, xylyl, chlorophenyl or anisyl.

BACKGROUND OF THE INVENTION

The utilization of $CO_2$ as a feedstock for the production of commodity chemicals potentially offers a more cost effective and renewable alternative to fossil fuel based carbon sources in the chemical industry. Unfortunately, the kinetic and thermodynamic stability of $CO_2$ has limited its exploitation thus far to a handful of commercial chemicals. One method to surmount this stability is the reduction of $CO_2$ via coupling to other relatively high energy small molecules. The functionalization of $CO_2$ with light olefins to produce α,β-unsaturated carboxylic acids is yet another intriguing target for this methodology, with potentially significant implications for the manufacture of acrylates used in superabsorbent polymers, elastomers, and detergents.

Transition metal promoted coupling of $CO_2$ and ethylene toward acrylate formation has been explored as an alternative to currently used propylene oxidation technology since the seminal reports of Hoberg and Carmona in the 1980's (Illustration 1). These pioneering investigators independently pursued new routes for $CO_2$-ethylene coupling using zerovalent nickel and group VI metals, respectively, though catalytic activity remained elusive.

Illustration 1. Reported $CO_2$-ethylene coupling at transitions metal complexes.

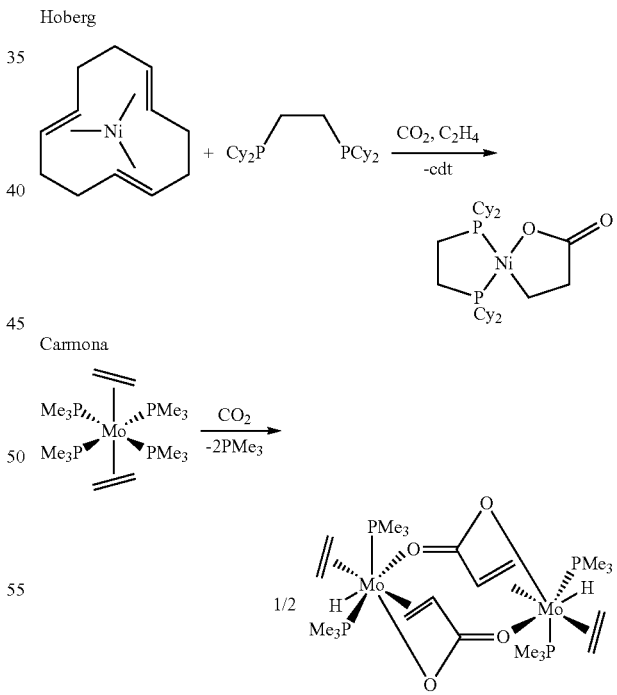

Limbach and co-workers have reported circumventing barriers to β-hydride elimination by adding external bases such as sodium tert-butoxide to diphosphine nickelalactone species which are believed to deprotonate the β-hydrogen directly without necessitating transfer of the hydride to nickel. This approach affords sodium acrylate ($NaCO_2CHCH_2$) in good yield and by repeated sequential additions of $CO_2$, ethylene and base several equivalents of sodium acrylate may be obtained in one reaction vessel. Unfortunately, the strong sodium base required for the deprotonation is not compatible with the high $CO_2$ pressure needed for nickelalactone formation, obviating catalytic production under a constant set of reaction conditions.

SUMMARY OF THE INVENTION

The Lewis acid tris(pentafluorophenyl)borane rapidly promotes ring opening β-hydride elimination in a 1,1'-bis(diphenylphosphino)ferrocene (dppf)nickelalactone complex under ambient conditions. The thermodynamic product of nickelalactone ring opening was characterized as (dppe)Ni(CH(CH$_3$)CO$_2$BAr$^f_3$). Without being bound by any particular theory, this is believed to be the result of β-hydride elimination and subsequent 2,1-insertion from a transient nickel(II) acrylate hydride intermediate. Without being bound by any particular theory it is believed that treatment of (dppe)Ni(CH(CH$_3$)CO$_2$BAr$^f_3$) with a nitrogen containing base afforded a diphosphine nickel(0) η$^2$-acryl borate adduct. (The Greek letter eta (η) references hapticity. η$^2$ describes a ligand binding through 2 contiguous atoms.) Formation of the diphosphine nickel(0) η$^2$-acryl borate adduct completes a net conversion of nickelalactone to acrylate species, a significant obstacle to catalytic acrylate production from $CO_2$ and ethylene. Displacement of the η$^2$-acrylate fragment from the nickel center was accomplished by addition of ethylene to yield a free acrylate salt and (dppf)Ni(η$^2$-C$_2$H$_4$).

In some embodiments this invention comprises the composition

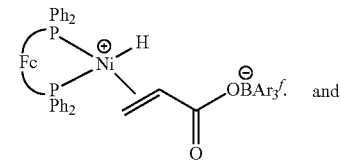
Structure I

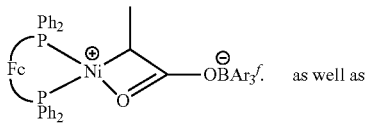
Structure Ia as well as

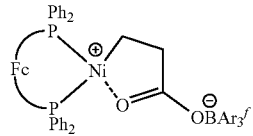
Structure Ib

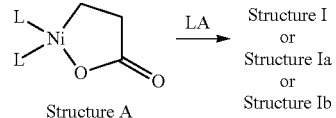
Structure X where Fc is ferrocene;
where Ph is a phenyl group
where P is phosphorus;

where Ar$^f$ is a fluorinated aryl substituent;
where B in BAr$^f_3$ is a boron linked to three fluorinated aryl substituents;
where aryl refers to a functional group or substituent derived from an aromatic ring; and,
where superscript f references a haloginated aryl, phenyl, naphthyl, thienyl, or indolyl with at least one halogen; and,
where R$^1$ is, for example, C$_1$-C$_{12}$-alkyl such as methyl, ethyl, 1-propyl, 2-propyl, 1-butyl, 2-butyl, 1-(2-methyl)propyl, 2-(2-methyl)propyl, 1-pentyl, 1-(2-methyl)pentyl, 1-hexyl, 1-(2-ethyl)hexyl, 1-heptyl, 1-(2-propyl)heptyl, 1-octyl, 1-nonyl, 1-decyl, 1-undecyl, 1-dodecyl, C$_3$-C$_{10}$-cycloalkyl which is unsubstituted or may bear a C$_1$-C$_4$-alkyl group, for example cyclopentyl, methylcyclopentyl, cyclohexyl, methylcyclohexyl, cycloheptyl, cyclooctyl and norbornyl, aryl which is unsubstituted or may bear one or two substituents selected from chlorine, C$_1$-C$_8$-alkyl and C$_1$-C$_8$-alkoxy, such as phenyl, napthyl, tolyl, xylyl, chlorophenyl or anisyl.

Yet further included is the method of manufacturing

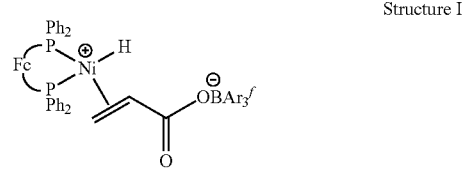
Structure I by the steps of reacting (dppf)nickelalactone with BAr$^f_3$.

The disclosed method of manufacturing producing structure I, Ia or Ib includes the steps of reacting a Lewis acid (LA) with (dppf)nickelalactone and BAr$^f_3$.

```
         LA       Structure I
Structure A  ──►      or
                  Structure Ia
                      or
                  Structure Ib
``` where L is selected from the group comprising butylamine, tri-n-pentylamine, tri-n-hexylamine, tri-n-heptylamine, tri-n-octylamine, tri-n-nonylamine, tri-n-decylamine, tri-n-undecylamine, tri-n-dodecylamine, tri-n-tridecylamine, tri-n-tetradecylamine, tri-n-pentadecylamine, tri-n-hexadecylamine, tri(2-ethylhexyl)amine, dimethyldecylamine, dimethyldodecylamine, dimethyltetradecylamine, ethyldi(2-propyl)amine, dioctylmethylamine, dihexylmethylamine, tricyclopentylamine, tricyclohexylamine, tricycloheptylamine, tricyclooctylamine, and the derivatives thereof substituted by one or more methyl, ethyl, 1-propyl, 2-propyl, 1-butyl, 2-butyl or 2-methyl-2-propyl groups, dimethylcyclohexylamine, methyldicyclohexylamine, diethylcyclohexylamine, ethyldicyclohexylamine, dimethylcyclopentylamine, methyldicyclopentylamine, triphenylamine, methyldiphenylamine, ethyldiphenylamine, propyldiphenylamine, butyldiphenylamine, 2-ethylhexyldiphenylamine, dimethylphenylamine, diethylphenylamine, dipropylphenylamine, dibutylphenylamine, bis-(2-ethylhexyl)phenylamine, tribenzylamine, methyldibenzylamine, ethyldibenzylamine and the derivatives thereof substituted by one or more methyl, ethyl, 1-propyl, 2-propyl, 1-butyl, 2-butyl or 2-methyl-2-propyl groups. $N-C_1$- to $-C_{12}$-alkylpiperidines, N,N'-di-$C_1$- to $-C_{12}$-alkylpiperazines, $N-C_1$- to $-C_{12}$-alkylpyrrolidines, $N-C_1$- to $-C_{12}$-alkylimidazoles, and the derivatives thereof substituted by one or more methyl, ethyl, 1-propyl, 2-propyl, 1-butyl, 2-butyl or 2-methyl-2-propyl groups, 1,4-diazabicyclo[2.2.2]octane (DABCO) N-methyl-8-azabicyclo[3.2.1]octane (tropane), N-methyl-9-azabicyclo[3.3.1]nonane (granatane), and 1-azabicyclo[2.2.2]octane (quinuclidine);

where LA comprises $BR^1R^2R^3$, Al $R^1R^2R^3$, or $LnX_2$ where Ln is a lanthanide. X is a halogen, triflate, or pseudohalide (each X need not be identical), and the Lewis acid further comprising inorganic cationic salts of sodium, lithium, potassium, cesium, magnesium, calcium, barium, strontium, or transition metal.

DETAILED DESCRIPTION OF THE INVENTION

This invention will be better understood with reference to the following definitions:

(a) Ferrocene (Fc) is an organometallic compound with the formula $Fe(C_5H_5)_2$;

(b) Ph shall reference a phenyl group. Thus $Ph_2$ references two phenyl groups.

(c) Structure I shall mean

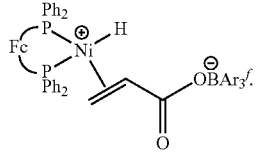

Structure I

Structure I is further expressed in the following configurations

Structure Ia shall mean

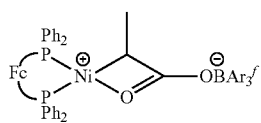

Structure Ia

Structure Ib shall mean

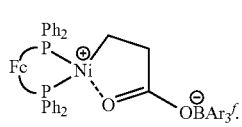

Ib

Structure X is Structure Ib with stated variables.

Structure X

"$Ar^f$" shall be understood to represent a fluorinated aryl substituent. $BAr^f_3$ shall mean a boron linked to three fluorinated aryl substituents. Aryl refers to any functional group or substituent derived from an aromatic ring, be it phenyl, naphthyl, thienyl, indolyl, etc. Fluorinated aryl shall mean phenyl, naphthyl, thienyl, or indolyl monosubstituted with at least one fluorine or other halogen. Particular reference is made to Structure X wherein the aryl moiety is pentafluorophenyl.

"DBU" shall mean 1,8-diazabicyclo[5.4.0]undec-7-ene.

"BTPP" shall mean tert-butylimino-tri(pyrrolidino)phosphorane.

1,1'-bis(diphenylphosphino)ferrocene nickelalactone or (dppf)Ni(CH$_2$CH$_2$CO$_2$) shall mean (dppf)nickelalactone

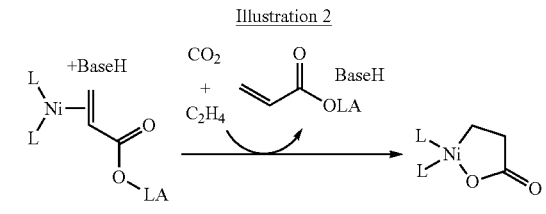

Illustration 2

In Illustration 2, L represents a ligand which may be of the formulas $PR^1R^2R^3$ (Formula 1);

$NR^1R^2R^3$ (Formula 2);

$R^4R^5P-E-PR^6R^7$ (Formula 3); and $R^4R^5N-E-NR^6R^7$ (Formula 4)

where $R^1, R^2, R^3, R^4, R^5, R^6, R^7$ are each independently $C_1$-$C_{12}$-alkyl, $C_3$-$C_{12}$-cycloalkyl, aryl, aryl-$C_1$-$C_4$-alkyl, where cycloalkyl, aryl and the aryl moiety of aryl-$C_1$-$C_1$-alkyl are unsubstituted or may bear 1, 2, 3 or 4 identical or different substituents, for example Cl, Br, I, F, $C_1$-$C_1$-alkyl or $C_1$-$C_4$-alkoxy.

Suitable $R^1, R^2, R^3, R^4, R^5, R^6, R^7$ radicals, for example, $C_1$-$C_{12}$-alkyl such as methyl, ethyl, 1-propyl, 2-propyl, 1-butyl, 2-butyl, 1-(2-methyl)propyl, 2-(2-methyl)propyl, 1-pentyl, 1-(2-methyl)pentyl, 1-hexyl, 1-(2-ethyl)hexyl, 1-heptyl, 1-(2-propyl)heptyl, 1-octyl, 1-nonyl, 1-decyl, 1-undecyl, 1-dodecyl, $C_3$-$C_{10}$-cycloalkyl which is unsubstituted or may bear a $C_1$-$C_4$-alkyl group, for example cyclopentyl, methylcyclopentyl, cyclohexyl, methylcyclohexyl, cycloheptyl, cyclooctyl and norbornyl, aryl which is unsubstituted or may bear one or two substituents selected from chlorine, $C_1$-$C_8$-alkyl and $C_1$-$C_8$-alkoxy, such as phenyl, napthyl, tolyl, xylyl, chlorophenyl or anisyl.

Suitable examples of the bridging group E for ligands of the formula 3 and 4 include for example, ethane, methane, or propane. Particular note is made to E being ferrocene.

In addition to the ligands described above, the catalyst may also have at least one further ligand which is selected from halides, amines, carboxylates, acetylacetonate, aryl- or alkylsulfonates, hydride, CO, olefins, dienes, cycloolefins, nitriles, aromatics and heteroaromatics, ethers, $PF_3$, phospholes, phosphabenzenes and mono-, di- and polydentate phosphinite, phosphonite, phosphoramidite and phosphite ligands.

Where base (Illustration 2) represents a deprotonating agent which may include an amine of the formula $N R^1 R^2 R^3$ (R's as defined above). By way of nonlimiting example, reference is made to Tri-n-propylamine, tri-n-butylamine, tri-n-pentylamine, tri-n-hexylamine, tri-n-heptylamine, tri-n-octylamine, tri-n-nonylamine, tri-n-decylamine, tri-n-undecylamine, tri-n-dodecylamine, tri-n-tridecylamine, tri-n-tetradecylamine, tri-n-pentadecylamine, tri-n-hexadecylamine, tri(2-ethylhexyl)amine. Additionally, dimethyldecylamine, dimethyldodecylamine, dimethyltetradecylamine, ethyldi(2-propyl)amine, dioctylmethylamine, dihexylmethylamine. Further, tricyclopentylamine, tricyclohexylamine, tricycloheptylamine, tricyclooctylamine, and the derivatives thereof substituted by one or more methyl, ethyl, 1-propyl, 2-propyl, 1-butyl, 2-butyl or 2-methyl-2-propyl groups. Yet further, dimethylcyclohexylamine, methyldicyclohexylamine, diethylcyclohexylamine, ethyldicyclohexylamine, dimethylcyclopentylamine, methyldicyclopentylamine. Noted too are triphenylamine, methyldiphenylamine, ethyldiphenylamine, propyldiphenylamine, butyldiphenylamine, 2-ethylhexyldiphenylamine, dimethylphenylamine, diethylphenylamine, dipropylphenylamine, dibutylphenylamine, bis-(2-ethylhexyl)phenylamine, tribenzylamine, methyldibenzylamine, ethyldibenzylamine and the derivatives thereof substituted by one or more methyl, ethyl, 1-propyl, 2-propyl, 1-butyl, 2-butyl or 2-methyl-2-propyl groups. N—$C_1$- to —$C_{12}$-alkylpiperidines, N,N'-di-$C_1$- to —$C_{12}$-alkylpiperazines, N—$C_1$- to —$C_{12}$-alkylpyrrolidines, N—$C_1$- to —$C_{12}$-alkylimidazoles, and the derivatives thereof substituted by one or more methyl, ethyl, 1-propyl, 2-propyl, 1-butyl, 2-butyl or 2-methyl-2-propyl groups. 1,4-diazabicyclo[2.2.2]octane (DABCO) N-methyl-8-azabicyclo[3.2.1]octane (tropane), N-methyl-9-azabicyclo[3.3.1]nonane (granatane), 1-azabicyclo[2.2.2]octane (quinuclidine).

The base may include association with a support material capable of absorbing hydrogen cations. In some embodiments attachments of the base options listed above are usefully attached to polystyrene beads as the support material.

Anionic bases (generally in the form of salts thereof with inorganic or organic ammonium ions or alkali metals or alkaline earth metals) or neutral bases. Inorganic anionic bases include carbonates, phosphates, nitrates or halides; examples of organic anionic bases include phenoxides, carboxylates, sulfates of organic molecular units, sulfonates, phosphates, phosphonates.

Organic neutral bases include primary, secondary or tertiary amines, and also ethers, esters, imines, amides, carbonyl compounds, carboxylates or carbon monoxide. Particular note is made to base being DBU, BTPP, or carbonate.

Where LA represents a Lewis Acid which may include: $BR^1R^2R^3$, Al $R^1R^2R^3$, $LnX_2$ where Ln includes any lanthanide metal and X includes any halogen, triflate, or pseudohalide. The Lewis Acid may include homogenous or supporting material capable of absorbing electrons from the reactor (e.g. polystyrene beads). The Lewis acid may also include inorganic cationic salts of, for example, sodium, lithium, potassium, cesium, magnesium, calcium, barium, strontium, or transition metal. Particular note is made to Lewis Acid being tris(pentafluorophenyl)borone.

Attention is drawn to the ability of a Lewis Acid to serve as an activator or co-catalyst for structures like A. Without being bound by any particular theory, it is believed this activation enables a cycle like the one above. This is significant because a Lewis acid activator permits a reaction without using a very strong base. Avoiding a strong base is advantageous since a strong base and $CO_2$ (used in making acrylate) are incompatible.

Without being bound by any particular theory, it is thought that the early (left side) and late (right side) transitional metal complexes likely share several common intermediates on the desired catalytic pathway, but are challenged by different steps in the proposed cycle (Illustration 2). In the case of group VI metals, the oxidative coupling of $CO_2$ and ethylene appears relatively facile.

Illustration 3

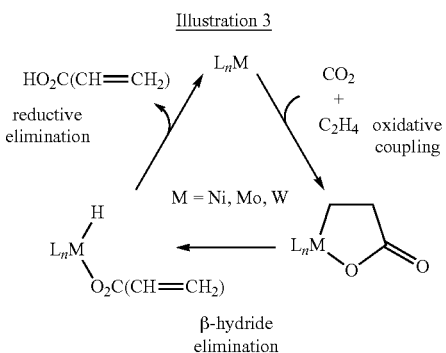

Catalytic cycle for production of acrylic acid from $CO_2$ and ethylene. occurring at ambient temperature and pressures. The couplings at molybdenum and tungsten have consistently afforded acrylate products, implying that β-hydride elimination from computationally predicted metalalactone intermediates is swift. Note that the subscript "n" in $L_n$ references number (not to be confused with LN meaning lanthanide).

Without being bound by any particular theory it is believed that the formation of Ia likely proceeds via β-hydride elimination from complex Ib to afford an unobserved nickel acrylate hydride intermediate (Illustration 3).

Illustration 4

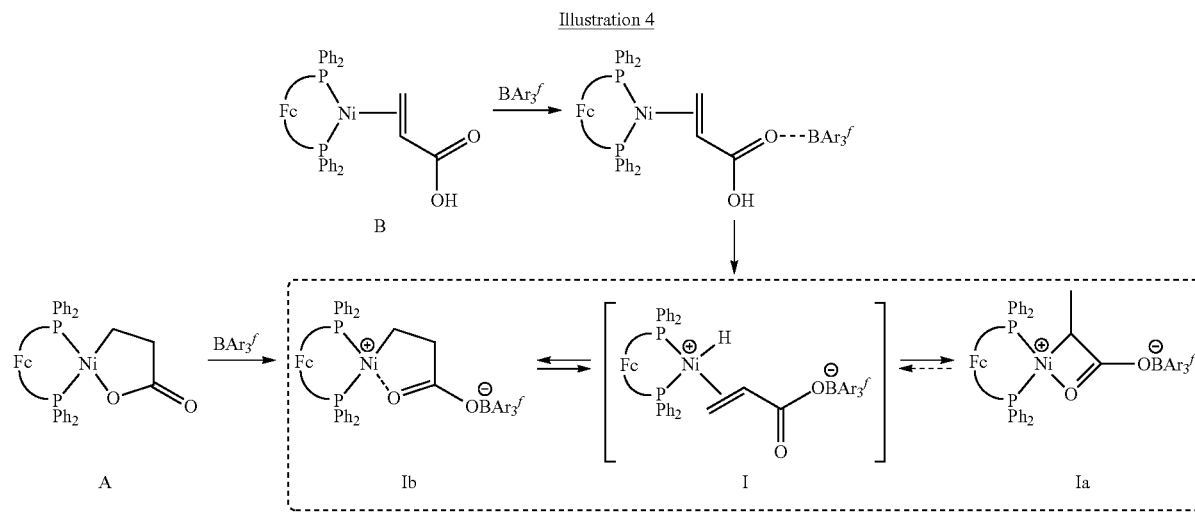

Subsequent 2,1-insertion of the acryl borate ligand would then produce the isolated compound Ia. Similar 2,1-insertions of acrylates into late transition metal hydrides have been reported by Brookhart and others. The ring-opened species Ia may alternatively be prepared by addition of $BAr^f_3$ to the $\eta^2$-acrylic acid complex, B (Illustration 3). Treatment of a benzene-$d_6$ solution of B with one equivalent of Lewis acid results in quick consumption of the starting material and formation of complexes Ib and Ia. This conversion is believed to occur via a short-lived intermediate ($t_{1/2}$~15 min). The intermediate was characterized only by NMR spectroscopy, and features a pair of doublet peaks in the $^{31}$P NMR spectrum at 23.42 and 33.42 ppm. The $^{19}$F NMR resonances at 165.7, −160.2 and −134.8 ppm are significantly shifted from those of free $BAr^f_3$ and are comparable to those observed in Ia, suggesting the complex contains a coordinated $BAr^f_3$ unit. In addition, the observation of a broad peak at 8.45 ppm in the $^1$H NMR spectrum, similar to the chemical shift of the —OH proton in B, suggests that this unstable intermediate is simply a borane adduct of the $\eta^2$-acrylic acid complex B (Illustration 3).

Lewis acid addition to B produces complexes Ia and Ib, believed simultaneously, with the mixture gradually shifting to solely Ia over 4 hours. This contrasts the sequential formation of Ib then Ia observed in $BAr^f_3$ addition to A, indicating that these two synthetic reactions enter the equilibrium process at different intermediates (Illustration 3). Our observations are most consistent with the reaction of B and $BAr^f_3$ affording the unobserved nickel(II) acrylate hydride species, which can then diverge to form complexes Ia and Ib with competitive rates of 1,2- and 2,1-insertion, respectively. Over time the reversible reaction equilibrates to the thermodynamically more stable 2,1-insertion product.

Deprotonation of Complex Ia. Having successfully induced β-hydride elimination from a stable nickelalactone species using a Lewis acid, experimental efforts were turned toward expelling acrylate from complex Ia. Deprotonation of Ia by neutral organic bases proved an effective method of accessing acrylate. Use of the sterically hindered phosphazene base, BTPP, resulted in the formation of the $\eta^2$-acrylate complex, 3 (equation 2). Note that BTPPH+ is the conjugate acid of BTPP and has a positive charge which balances the negative charge on complex 3 in equation 2.

Illustration 5

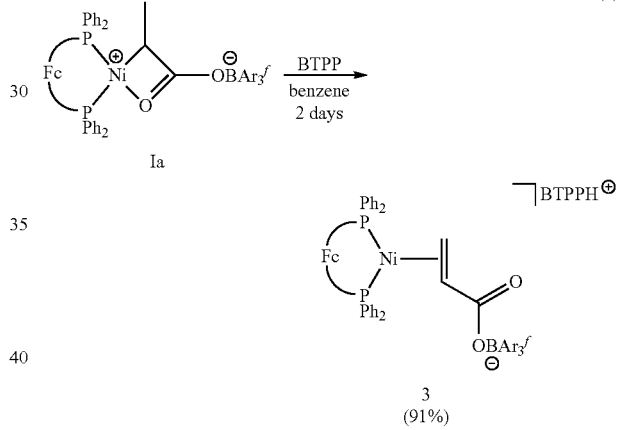

(2)

over two days at ambient temperature. Complex 3 exhibited limited solubility in hydrocarbon solvents, but proved modestly soluble in ethereal and halogenated solvents. The $^1$H NMR spectrum of a chlorobenzene-$d_5$ solution of 3 displays resonances at 2.06, 3.16 and 3.49 ppm assigned as the vinylic protons of the bound olefin. The assignments were confirmed by $^1$H-$^{13}$C HSQC NMR experiments which indicate correlations to $^{13}$C chemical shifts at 46.30 ($CH_2$) and 52.45 (CH) ppm. These resonances are analogous to those reported for the $\eta^2$-acrylic acid complex B. The $^1$H NMR spectrum of 3 also exhibits the expected peaks for the conjugate acid of BTPP, including a broad N—H resonance at 4.75 ppm. The $^{31}$P NMR spectrum completed the characterization with two doublets at 19.8 and 29.6 ppm assigned to the dppf ligand, as well as a singlet at 23.1 ppm from [BTPPH]+. Addition of slightly weaker bases including DBU to complex Ia is believed to have promted some acrylate formation, although in the case of this bicyclic amine, the $\eta^2$-acrylate complex was not formed as selectively. Addition of 1 eq of DBU to complex Ia over 2 days produced a mixture of the free $[H_2C=CHCO_2BAr^f_3]^-$ [DBU]+ salt, a complex analogous to 3, and some free dppf ligand. $[H_2C=CHCO_2BAr^f_3]^-$ [DBU]+ and $[H_2C=CHCO_2BAr^f_3]^-$ [BTPPH]+ salts were identified by NMR spectroscopy against independently prepared salts synthesized through the reaction of acrylic acid with base and $BAr_3^f$.

The observed deprotonation of Ia with BTPP and DBU stands in contrast to the reactivity of nickelalactone A, which similar to other diphosphine nickelacycles, is believed to requires stronger bases to induce elimination. Without being bound by any particular theory, it is believed that the role of Lewis acid in facilitating nickelalactone deprotonation by more mild bases is of significance to the larger challenge of catalytic acrylate production from $CO_2$ and ethylene. As discussed above, several nickel compounds have been reported as capable of coupling $CO_2$-ethylene into nickelalatone species at elevated pressures. However, inducing elimination to produce acrylate in a fashion compatible with the presence of excess $CO_2$ has remained a persistent barrier. The ability to use more mild bases for acrylate liberation enhances the viability of deprotonation techniques to overcome this barrier under high $CO_2$ pressure. The use of $CO_2$ compatible bases such as carbonates in conjunction with mild Lewis acids or frustrated Lewis pairs allows for a practical catalytic production of acrylate.

The technique of Lewis acid induced elimination from nickel lactones described here is applicable to other ligand platforms for $CO_2$-ethylene coupling.

Lewis acid, tris(pentafluorophenyl)borane, has been found to promote rapid β-hydride elimination from an isolable nickelalactone species, $(dppf)Ni(CH_2CH_2CO_2)$, under ambient conditions. The reversible β-hydride elimination ultimately results in formation of thermodynamically stable 2,1-acryl borate insertion product, $(dppe)Ni(CH(CH_3)CO_2BAr^f_3)$ (2). Without being bound by any particular theory, it is believed that the Lewis acid activation renders 2 more facile toward deprotonation by external base than the starting nickelalactone species. Treatment of 2 with nitrogen containing bases formed either a free acrylate salt or an $\eta^2$-acrylate coordination complex with the nickel. Coordinated borate substituted acrylate may be substituted by ethylene.

EXPERIMENTAL

General Considerations.

All manipulations were carried out using standard vacuum, Schlock, cannula, or glovebox techniques. Ethylene was purchased from Corp Brothers and stored over 4 Å molecular sieves in heavy walled glass vessels prior to use. Argon and nitrogen were purchased from Corp Brothers and used as received. Both $(dppf)Ni(CH_2CH_2CO_2)$ (A) and $(dppf)Ni(CH_2=CHCO_2H)$ (B) were prepared according to literature procedure. All other chemicals were purchased from Aldrich, VWR, Strem, Fisher Scientific or Cambridge Isotope Laboratories. Volatile, liquid chemicals were dried over 4 Å molecular sieves and distilled prior to use. Solvents were dried and deoxygenated using literature procedures.

$^1H$, $^{13}C$, $^{19}F$ and $^{31}P$ NMR spectra were recorded on Bruker DRX 400 Avance (Billerica, Mass.) and 300 Avance MHz spectrometers. $^1H$ and $^{13}C$ chemical shifts are referenced to residual solvent signals; $^{19}F$ and $^{31}P$ chemical shifts are referenced to the external standards $C_6H_5CF_3$, and $H_3PO_4$, respectively. Probe temperatures were calibrated using ethylene glycol and methanol as previously described. Unless otherwise noted, all NMR spectra were recorded at 23° C. IR spectra were recorded on a Jasco 4100 FTIR spectrometer. GC-MS data were recorded using a Hewlett-Packard (Agilent) GCD 1800C GC-MS spectrometer. X-ray crystallographic data were collected on a Bruker D8 QUEST diffractometer. Samples were collected in inert oil and quickly transferred to a cold gas stream. The structures were solved from direct methods and Fourier syntheses and refined by full-matrix least-squares procedures with anisotropic thermal parameters for all non-hydrogen atoms. Elemental analyses were performed at Robertson Microlit Laboratories, Inc., in Madison, N.J. or Atlantic Microlab, Inc., in Norcross, Ga.

Preparation of $(dppf)Ni(CH_2CH_2CO_2B(C_6F_5)_3)$ (Ib)

Example 1

A 20 mL scintillation vial was charged with 0.013 g (0.019 μmol) $(dppf)Ni(CH_2CH_2CO_2)$ (A), 0.010 g (0.019 μmol) of $B(C_6F_5)_3$ and approximately 2 mL of $CH_2Cl_2$. The deep orange solution was stirred for 5 minutes and the volatiles removed under vacuum. The resulting solid was then dissolved in $C_6D_6$ for NMR study. Identical NMR spectra may be taken at 10° C. to slow the conversion of Ib to Ia for longer timescale experiments. $^1H$ NMR ($C_6D_6$): δ 0.84 (m, 2H, Ni-α-$CH_2$), 2.21 (m, 2H, Ni-β-$CH_2$), 3.36 (s, 2H, CpH), 3.62 (s, 2H, CpH), 3.72 (s, 2H, CpH), 4.12 (s, 2H, CpH), 6.98-7.67 (Ph). $^{31}P\{^1H\}$ NMR ($C_6D_6$): δ 15.7 (d, $^2J_{P,P}$ 15.8 Hz, 1P, $PPh_2$), 34.3 (d, $^2J_{P,P}$ 15.8 Hz, 1P, $PPh_2$). $^{19}F$ NMR ($C_6D_6$): δ −166.60 (t), −161.47 (t), −135.77 (d).

A basic process of preparing Ib comprises the steps of
(a) combining an organometallic compound such as (dppf)$Ni(CH_2CH_2CO_2)$, a Lewis acid such as $B(C_6F_5)_3$ and, a solvent such as $CH_2Cl_2$;
(b) stirring for from about 1 to about 5 minutes;
(c) removing volatiles under vacuum. Ib precipitates out as a solid.

Preparation of Other Embodiments of Ib

Example 2

A 20 mL scintillation vial is charged with 0.019 μmol of $(dppe)Ni(CH_2CH_2CO_2)$ (A) (where dppe is 1,2-Bis(diphenylphosphino)ethane), 0.019 μmol of $B(C_6F_5)_3$ and approximately 2 mL of $CH_2Cl_2$, chlorobenzene, or other polar solvent. The solution is stirred for 5 minutes-12 hours and the volatiles removed under vacuum. The resulting solid 1b is then dissolved in organic solvent for NMR study or use.

Preparation of Other Embodiments of Ib

Example 3

A 20 mL scintillation vial is charged with 0.019 μmol of $(PMe_3)_2Ni(CH_2CH_2CO_2)$ (A) (where $PMe_3$ is trimethylphosphine), 0.019 μmol of $B(C_6F_5)_3$ and approximately 2 mL of $CH_2Cl_2$, chlorobenzene, or other polar solvent. The solution is stirred for 5 minutes-12 hours and the volatiles removed under vacuum. The resulting solid 1b is then dissolved in organic solvent for NMR study or use.

Preparation of $(dppf)Ni(CH(CH_3)(CO_2B(C_6F_5)_3)$ (Ia)

Example 1

A 20 mL container was charged with 0.096 g (0.142 μmol) $(dppf)Ni(CH_2=CHCO_2H)$ (B), 0.073 g (0.143 μmol) of $B(C_6F_5)_3$ and approximately 5 mL of toluene. The orange solution was stirred for one day and the volatiles removed under vacuum. The resulting solid was washed with 2 mL of pentane, extracted with diethyl ether, and chilled at −35° C. to afford 128 mg (76%) of Ia as orange crystals. Anal. Calcd. for $C_{55}H_{32}BF_{15}FeNiO_2P_2$: C, 55.18; H, 2.69. Found: C, 55.50; H, 2.67. $^1H$ NMR ($C_6D_6$): δ 0.23 (dd, 3H, $CH_3$, $J_{H,H}$ 7.0 Hz, $J_{P,H}$ 7.8 Hz, Ni-β-$CH_3$), 2.03 (m, 1H, Ni-α-CH), 3.59 (s, 1H, CpH), 3.67 (s, 1H, CpH), 3.71 (s, 1H, CpH), 3.73 (s, 2H, CpH), 3.81 (s, 1H, CpH), 4.05 (s, 1H, CpH), 4.35 (s, 1H, CpH), 6.91-7.11 (m, 12H, CpH), 7.34-7.39 (m, 2H, Ph), 7.51-7.59 (m, 4H, Ph), 7.67-7.70 (m, 2H, Ph). $^{31}P\{^1H\}$ NMR ($C_6D_6$): δ 22.4 (d, $^2J_{P,P}$ 20.0 Hz, 1P, $PPh_2$), 36.2 (d, $^2J_{P,P}$ 20.0 Hz, 1P, $PPh_2$), $^{13}C\{^1H\}$ NMR ($C_6D_6$): δ 12.36 (Ni—CH—$CH_3$), 34.58 (Ni—CH), 73.36, 74.81, 75.04, 75.40, 76.18 (Cp), 128.66-129.15, 131.36, 133.03, 133.15, 133.85, 133.98, 133.12, 134.12, 134.24, 134.74, 134.86 (aryl) 181.20 ($CO_2$). $^{19}F$ NMR ($C_6D_6$): δ −166.60 (t), −161.02 (t), −135.37 (d). IR (KBr): $v_{C=O}$=1644 $cm^{-1}$.

Preparation of Other Embodiments of Ia

Example 2

A 20 mL scintillation vial is charged with 0.142 μmol of (dppe)Ni($CH_2$=$CHCO_2H$) (B) (where dppe is 1,2-Bis (diphenylphosphino)ethane), 0.143 μmol of $B(C_6F_5)_3$ and approximately 5 mL of toluene, $CH_2Cl_2$, chlorobenzene, or other polar solvent. The solution is stirred for one day to one week. After that the volatiles are removed under vacuum. The resulting solid is washed with 2 mL of pentane, diethyl ether, or toluene to afford Ia as solid.

Preparation of Other Embodiments of Ia

Example 3

A 20 mL scintillation vial is charged with 0.142 μmol of $(PMe_3)_2Ni(CH_2=CHCO_2H)$ (B) (where $PMe_3$ is trimethylphosphine), 0.143 μmol of $B(C_6F_5)_3$ and approximately 5 mL of toluene, $CH_2Cl_2$, chlorobenzene, or other polar solvent. The solution is stirred for one day to one week and the volatiles removed under vacuum. The resulting solid is washed with 2 mL of pentane, diethyl ether, or toluene to afford Ia as solid.

Preparation of [(dppf)Ni($\eta^2$-$CH_2$=CH—$CO_2B$ $(C_6F_5)_3$)][HBTPP] (B)

Example 1

A 20 mL scintillation vial was charged with 0.035 g (0.029 μmol) of (dppf)Ni(CH($CH_3$)($CO_2B(C_6F_5)_3$)) (Ia), 9 μL (0.029 μmol) of BTPP and approximately 1 mL of benzene. The solution was stirred for two days resulting in precipitation of a yellow solid. The solid was collected by filtration to afford 40 mg (91%) of 3 as a yellow powder. The material may be extracted with THF if necessary to remove trace nickel metal particulates. Anal. Calcd. for $C_{71}H_{65}BF_{15}FeNiN_4O_2P_3$: C, 56.49; H, 4.34; N, 3.71. Found: C, 55.96; H, 4.48; N, 3.51. $^1H$ NMR ($C_6D_5Cl$): δ 0.97 (s, 9H, N—C($CH_3$)$_3$), 1.39 (s, 12H, N-β-$CH_2$), 2.06 (m, 1H, $\eta^2$-$CH_2$=CH), 2.70 (s, 12H, N-α-$CH_2$), 3.16 (m, 1H, $\eta^2$-$CH_2$=CH), 3.49 (m, 1H, $\eta^2$-$CH_2$=CH), 3.79 (s, 1H, CpH), 3.89 (s, 1H, CpH), 3.96 (m, 1H, CpH), 3.99 (s, 1H, CpH), 4.02 (s, 2H, CpH), 4.47 (s, 1H, CpH), 4.62 (s, 1H, CpH), 4.75 (br, 1H, NH) 6.92-7.24 (m, 12H, Ph), 7.56-7.99 (m, 8H, Ph). $^{31}P\{^1H\}$ NMR ($C_6D_5Cl$): δ 19.8 (d, $^2J_{P,P}$ 22.8 Hz, 1P, $PPh_2$), 23.1 (s, 1P, [HBTPP]$^+$), 29.6 (d, $^2J_{P,P}$ 22.8 Hz, 1P, $PPh_2$). $^{13}C\{^1H\}$ NMR ($C_6D_5Cl$): δ 26.01 (N-β-$CH_2$), 30.93 (N—C($CH_3$)$_3$), 46.30 ($\eta^2$-$CH_2$=CH), 47.40 (N-α-$CH_2$), 52.45 ($\eta^2$-$CH_2$=CH), 70.09, 70.44, 72.62, 73.03, 73.46, 74.78, 74.90 (Cp), 127.55, 131.50, 131.94, 133.47, 135.05, 136.03, 136.38, 147.80, 149.37 (aryl) three aryl signals not located, 178.33 ($CO_2$). $^{19}F$ NMR ($C_6D_5Cl$): δ −134.00 (d), −164.42 (t), −168.24 (t). IR (KBr): $v_{C=O}$=1642 $cm^{-1}$.

Preparation of Other Embodiments of B

Example 2

A 20 mL scintillation vial is charged with 0.029 μmol of (dppe)Ni(CH($CH_3$)($CO_2B(C_6F_5)_3$)) (Ia), (where dppe is 1,2-Bis(diphenylphosphino)ethane) 9 μL (0.029 μmol) of BTPP and approximately 1 mL of benzene, toluene, chlorobenzne or other organic solvent. The solution is stirred for two days to one week. The solvent is removed and the solid collected. Extraction and filtration with benzene, toluene, chlorobenzne or other organic solvent is used to remove trace nickel metal particulates if present.

Preparation of Other Embodiments of B

Example 3

A 20 mL scintillation vial is charged with 0.029 μmol of $(PMe_3)_2Ni$(CH($CH_3$)($CO_2B(C_6F_5)_3$)) (Ia), (where $PMe_3$ is trimethylphosphine)) 9 μL (0.029 μmol) of BTPP and approximately 1 mL of benzene, toluene, chlorobenzne or other organic solvent. The solution is stirred for two days to one week. The solvent is removed and the solid collected. Extraction and filtration with benzene, toluene, chlorobenzne or other organic solvent is used to remove trace nickel metal particulates if present.

The following publications are noted. These, and all references cited Herein, are incorporated by reference in their entirety.

1. *Renewable Raw Materials: New Feedstocks for the Chemical Industry*; Ulber, R.; Sell, D.; Hirth, T. Eds; Wiley-VCH: Weinheim, 2011.
2. Vennestrom, P. N. R.; Osmundsen, C. M.; Christensen, C. H.; Tarning, E. *Angew. Chem. Int. Ed. Engl.* 2011, 50, 10502.
3. Huang, K.; Sun, C-L.; Shi, Z-J. *Chyem. Soc. Rev.* 2011, 40, 2435.
4. *Carbon Dioxide as a Chemical Feedstock*, Aresta, M. Ed.; Wiley-VCH: Weinheim, 2010.
5. Aresta, M. Dibenedetto. A. Industrial Utilization of Carbon Dioxide. In *Developments and Innovation in Carbon Dioxide Capture and Storage Technology*. M. M. Maroto-Valer, Ed.; Woodhead: Cambridge, 2010, pp. 377-410.
6. *Feedstocks for the Future*; Bozell, J.; Patel, M. K. Eds.; ACS Symposium Series 921; American Chemical Society; Washington, D.C., 2006.
7. Tolman, W. B. *Carbon Dioxide Reduction and Uses as a Chemical Feedstock. Activation of Small Molecules: Organometallic and Bioinorganic Perspectives*, Wiley-VCH: Weinheim, 2006; pp. 1-35.
8. Quadrelli, E. A.; Centi, G.; Duplan, J-L.; Perathoner, S. *ChemSusChem*, 2011, 4, 1194.
9. Cokoja, M.; Bruckmeier, C.; Rieger, B.; Herrmann, W. A.; Kuhn, F. E. *Angew. Chem. Int. Ed.* 2011, 50, 8510.
10. Sakakura, T.; Choi, J-C.; Yasuda, H. *Chem. Rev.* 2007, 107, 2365.

11 Darensbourg, D. J. *Inorg. Chem.* 2010, 49, 10765-10780. Aresta, M.; Dibenedetto, A. *Dalton Trans.* 2007, 2975.
12. Aresta, M. Dibenedetto, A. *Catal. Today* 2004, 98, 455.
13. Patil, Y.; Tambade, P. J.; Jagtap, S. R.; Bhanage, B. M. *Front. Chem. Eng. China* 2010, 4, 213.
15. Hoberg, H.; Schaefer, D. J. *Organomet. Chem.* 1983, 251, C51.
16. Alvarez, R.; Carmona, E.; Cole-Hamilton, D. J.; Galindo, A.; Gutierrez-Puebla, E.; Monge, A.; Poveda, M. L.; Ruiz, C. *J. Am. Chem. Soc.* 1985, 107, 5529.
17. Hoberg, H.; Ballesteros, A.; Sigan, A.; Jegat, C.; Barhausen, D.; Milchereit, A. *J. Organomet. Chem.* 1991, 407, C23.
18 Hoberg, H.; Ballesteros, A. *J. Organomet. Chem.* 1991, 411, C11.
19. Hoberg, H.; Peres, Y.; Kruger, C.; Tsay, Y. H. *Angew. Chem. Int Ed. Engl.* 1987, 26, 771.
20. Hoberg, H.; Schafer, *J. Organomet. Chem.* 1983, 251, C51.
21. Alvarez, R.; Carmona, E.; Galindo, A.; Gutierrez, E.; Marin, J. M.; Monge, A.; Poveda, M. L.; Ruiz, C.; Savariault, J. M. *Organometallics* 1989, 8, 2430.
22. Galindo, A.; Pastor, A.; Perez, P.; Carmona, E. *Organometallics* 1993, 12, 4443. c) Collazo, C.; del Mar Conejo, M.; Pastor, A.; Galindo, A. *Inorg. Chim. Acta.* 1998, 272, 125.
23. Bernskoetter, W. H.; Tyler, B. T. *Organometallics,* 2011, 30, 520.
24. Graham, D. C.; Mitchell, C.; Bruce, M. I.; Metha, G. F.; Bowie, J. H.; Buntine, M. A. *Organometallics* 2007, 26, 6784.
25. Papai, I.; Schubert, G.; Mayer, I.; Besenyei, G.; Aresta, M. *Organometallic* 2004, 23, 5252. d) Schubert, G.; Papai, I. *J. Am. Chem. Soc.* 2003, 125, 14847.
26. Sakaki, S.; Mine, K.; Hamada, T.; Arai, T. *Bull. Chem. Soc. Jpn.* 1995, 68, 1873.
27. Sakaki, S.; Mine, K.; Taguchi, D.; Arai, T. *Bull. Chem. Soc. Jpn.* 1993, 66, 3289.
28. Dedieu, A.; Ingold, F. *Angew. Chem., Int. Ed. Engl.* 1989, 28, 1694.
29. Wolfe, J. M.; Bernskoetter, W. H. *Dalton Trans.* 2012, 41, 10763.
30. Doherty, M. D.; Grant, B.; White, P. S.; Brookhart M. *Organometallics* 2007, 26, 5950.
31. Yi, C. S.; Liu, N. *J. Organomet. Chem.* 1998 553, 157.
32. Brookhart, M.; Hauptman, E. *J. Am. Chem. Soc.* 1992, 114, 4437.
33. Berkefeld, A.; Drexler, M.; Moller, H. M.; Mecking, S. *J. Am. Chem. Soc.* 2009, 131, 12613.
34. Liang, L-C.; Chien, P-S.; Lee, P-Y. *Organometallics* 2008, 27, 3082.
35. Jones, G. D.; Vicic, D. A. *Organometallics* 2005, 24, 3881.
36. Garcia, J. J.; Arevalo, A.; Brunkan, N. M.; Jones, W. D. *Organometallics* 2004, 23, 3997.
37. Bennett, M. A.; Johnsom, J. A.; Willis, A. C. *Organometallics* 1996, 15, 68.
38. Selingson, A. L.; Cowan, R. L.; Trogler, W. C. *Inorg. Chem.* 1991, 30, 3371.
39. Tolman, C. A.; Seidel, W. C.; Gerlach, D. H. *J. Am. Chem. Soc.* 1972, 94, 2669.
40. Pangborn, A. B.; Giardello, M. A.; Grubbs, R. H.; Rosen, R. K.; Timmers, F. J *Organometallics* 1996, 15, 1518.
41. Sandström, J. *Dynamic NMR Spectroscopy*; Academic Press: New York, 1982.

The invention claimed is:
1. The composition

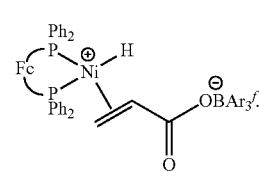

Structure I where Fc is ferrocene;
where P is phosphorus
where Ph is a phenyl group;
where $Ar^f$ is a fluorinated aryl substituent;
where B in $BAr^f_3$ is a boron linked to three fluorinated aryl substituents;
where aryl refers to a functional group or substituent derived from an aromatic ring; and,
where superscript f references a haloginated aryl, phenyl, naphthyl, thienyl, or indolyl.

2. The composition of claim 1 wherein said $Ar^f_3$ is pentafluorophenyl.

3. The composition of claim 1 in the configuration

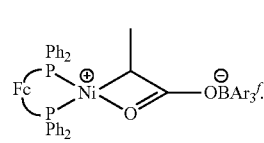

Structure Ia

4. The composition of claim 1 in the configuration

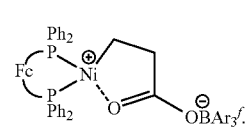

Structure Ib

5. The composition of the structure

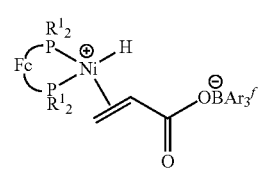

Structure X where Fc is ferrocene;
where P is phosphorus
where $R^1$ is $C_1$-$C_{12}$ alkyl, $C_3$-$C_{10}$-cycloalkyl which is unsubstituted or may bear a $C_1$-$C_4$-alkyl group, or aryl which is unsubstituted or may bear one or two substituents selected from chlorine, $C_1$-$C_8$-alkyl and $C_1$-$C_8$-alkoxy;
where $Ar^f$ is a fluorinated aryl substituent;
where B in $BAr^f_3$ is a boron linked to three fluorinated aryl substituents;
where aryl refers to a functional group or substituent derived from an aromatic ring; and, where superscript f references a haloginated aryl, phenyl, naphthyl, thienyl, or indolyl.

6. A method of manufacturing producing structure I, Ia or Ib by the steps of reacting a Lewis acid (LA) with (L)nickelalactone and BAr$^f_3$;

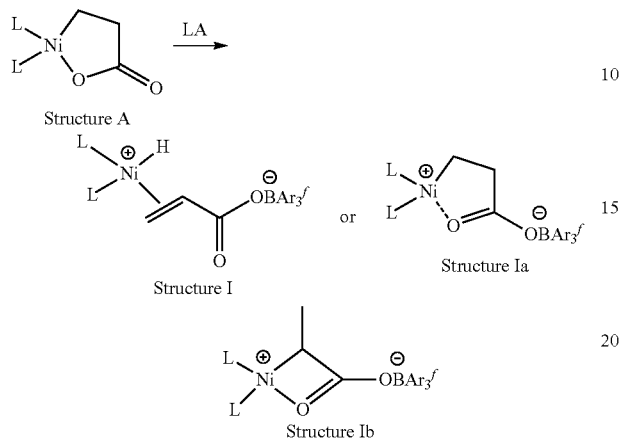

where L is selected from the group comprising 1,1'-bis(diphenylphosphino)ferrocene (dppf), butylamine, tri-n-pentylamine, tri-n-hexylamine, tri-n-heptylamine, tri-n-octylamine, tri-n-nonylamine, tri-n-decylamine, tri-n-undecylamine, tri-n-dodecylamine, tri-n-tridecylamine, tri-n-tetradecylamine, tri-n-pentadecylamine, tri-n-hexadecylamine, tri(2-ethylhexyl)amine, dimethyldecylamine, dimethyldodecylamine, dimethyltetradecylamine, ethyldi(2-propyl)amine, dioctylmethylamine, dihexylmethylamine, tricyclopentylamine, tricyclohexylamine, tricycloheptylamine, tricyclooctylamine, and the derivatives thereof substituted by one or more methyl, ethyl, 1-propyl, 2-propyl, 1-butyl, 2-butyl or 2-methyl-2-propyl groups; dimethylcyclohexylamine, methyldicyclohexylamine, diethylcyclohexylamine, ethyldicyclohexylamine, dimethylcyclopentylamine, methyldicyclopentylamine, triphenylamine, methyldiphenylamine, ethyldiphenylamine, propyldiphenylamine, butyldiphenylamine, 2-ethylhexyldiphenylamine, dimethylphenylamine, diethylphenylamine, dipropylphenylamine, dibutylphenylamine, bis-(2-ethylhexyl)phenylamine, tribenzylamine, methyldibenzylamine, ethyldibenzylamine and the derivatives thereof substituted by one or more methyl, ethyl, 1-propyl, 2-propyl, 1-butyl, 2-butyl or 2-methyl-2-propyl groups, N—$C_1$- to —$C_{12}$-alkylpiperidines, N,N'-di-$C_1$- to —$C_{12}$-alkylpiperazines, N—$C_1$- to —$C_{12}$-alkylpyrrolidines, N—$C_1$- to —$C_{12}$-alkylimidazoles, and the derivatives thereof substituted by one or more methyl, ethyl, 1-propyl, 2-propyl, 1-butyl, 2-butyl or 2-methyl-2-propyl groups, 1,4-diazabicyclo[2.2.2]octane (DABCO) N-methyl-8-azabicyclo[3.2.1]octane (tropane), N-methyl-9-azabicyclo[3.3.1]nonane (granatane), 1-azabicyclo[2.2.2]octane (quinuclidine); and where LA comprises BR$^1$R$^2$R$^3$, Al R$^1$R$^2$R$^3$, or LnX$_2$ where Ln is a lanthanide;
X is a halogen, triflate, or pseudohalide (each X need not be identical), and
the Lewis acid further comprising inorganic cationic salts of sodium, lithium, potassium, cesium, magnesium, calcium, barium, strontium, or transition metal.

7. The composition of claim 5 wherein
where R$^1$ is selected from the group consisting of methyl, ethyl, 1-propyl, 2-propyl, 1-butyl, 2-butyl, 1-(2-methyl)propyl, 2-(2-methyl)propyl, 1-pentyl, 1-(2-methyl)pentyl, 1-hexyl, 1-(2-ethyl)hexyl, 1-heptyl, 1-(2-propyl)heptyl, 1-octyl, 1-nonyl, 1-decyl, 1-undecyl, and 1-dodecyl.

8. The Composition of claim 5 wherein said $C_3$-$C_{10}$-cycloalkyl is selected from the group consisting of cyclopentyl, methylcyclopentyl, cyclohexyl, methylcyclohexyl, cycloheptyl, cyclooctyl and norbornyl.

9. The composition of claim 5 wherein said aryl is selected from the group consisting of phenyl, napthyl, tolyl, xylyl, chlorophenyl and anisyl.

* * * * *